United States Patent
Chen et al.

(10) Patent No.: US 7,703,979 B2
(45) Date of Patent: Apr. 27, 2010

(54) RADIATION DEVICE FOR HUMAN BODY INSPECTION

(75) Inventors: Zhiqiang Chen, Beijing (CN); Yinong Liu, Beijing (CN); Ziran Zhao, Beijing (CN); Lian Wang, Beijing (CN); Lan Zhang, Beijing (CN); Yumin Yi, Beijing (CN); Jinyu Zhang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 12/349,445

(22) Filed: Jan. 6, 2009

(65) Prior Publication Data

US 2009/0180593 A1  Jul. 16, 2009

(30) Foreign Application Priority Data

Jan. 11, 2008  (CN) .................... 2008 1 0056059

(51) Int. Cl.
*H05G 1/06* (2006.01)
*H05G 1/02* (2006.01)
(52) U.S. Cl. ..................... 378/194; 378/193
(58) Field of Classification Search ............ 378/189, 378/193–197
See application file for complete search history.

(56) References Cited

U.S. PATENT DOCUMENTS

| 1,400,333 | A | * | 12/1921 | Waite | 378/194 |
| 2,060,981 | A | * | 11/1936 | Fischer et al. | 378/194 |
| 4,136,284 | A | * | 1/1979 | Blumental | 378/11 |
| 5,438,603 | A | * | 8/1995 | Schonartz | 378/39 |

* cited by examiner

*Primary Examiner*—Irakli Kiknadze
(74) *Attorney, Agent, or Firm*—Knobbe Martens Olson & Bear LLP

(57) ABSTRACT

Disclosed is a radiation device for the human body inspection. The device includes a X-ray generator for radiating radiation; a detector for receiving the radiation radiated from the X-ray generator; a first flexible member connected with the X-ray generator for hoisting the X-ray generator; a second flexible member connected with the detector for hosing the detector; and a driving device for synchronically driving the X-ray generator and the detector through the first and second flexible members, and at the same time, the X-ray generator and the detector are spaced from each other a predetermined distance in a horizontal direction. The radiation device for the human body inspection according to the present invention can ensure that the radiation source and the detector can be operated synchronically during the whole inspection process; thereby the quality of radiation imaging is increased. Furthermore, the radiation device for the human body inspection according to the present invention is allowed to save cost and reduce noise.

5 Claims, 2 Drawing Sheets

RADIATION DEVICE FOR HUMAN BODY INSPECTION

CROSS REFERENCE TO RELATED APPLICATIONS

This application claims priority under 35 U.S.C. Section 119 to Chinese Application 200810056059.7, filed on Jan. 11, 2008. This application is hereby incorporated by reference in its entirety.

FIELD OF INVENTION

The present invention relates to a radiation device for the human body inspection.

BACKGROUND OF INVENTION

There is a higher demand on the modern security defense equipments due to that the international terrorism and criminal activities have become increasingly rampant, more particularly, the demand on the equipment for inspecting dangerous substances and weapons hidden in the cloth, body or within the body becomes more urgent.

In addition to the metal substances, if the exploder or weapons in plastic and ceramic are also listed in the investigation and scanning scope, only X-ray imaging method, that is, a modern digital X-ray imaging method can be used to satisfy the above requirements. Apparently, metal detectors for the human body inspection widely used at present are far short of the demand on fighting against terrorism, which only can detect the existence of the metal, but the location and the shape thereof are unable to determined, those plastic explosives and weapons only can be discovered by means of manual touching. Also, various types of electric "nose" are ineffective for those plastic weapon and explosives with tight package. In other words, the conventional human body inspection method is not only low in efficiency, but also having inconvenience and light disrespect for those involved people.

During the process of X-ray radiation imaging for the human body inspection, people are generally moved, but the X-ray generator and the detector are still. However, under the situation where the people being inspected are moved, collected images may become false images which will extremely affect the image quality, particularly definition of the image.

SUMMARY OF INVENTION

Bearing in mind of the above shortages in prior arts, an object of the present invention is to provide a radiation device for the human body inspection, which at least alleviates above overcomes.

According to one aspect of the present invention, the present invention provides a radiation device for the human body inspection, including: a X-ray generator for radiating the radiation; a detector for receiving the radiation radiated from the X-ray generator; a first flexible member connected with the X-ray generator, for hoisting the X-ray generator; a second flexible member connected with the detector, for hoisting the detector; and a driving device for synchronously driving the X-ray generator and the detector through the first and second flexible members, and at the same time, the X-ray generator and the detector are spaced away from each other in a predetermined distance in a horizontal direction.

By employing above structure, the X-ray generator of the radiation device and the detector are able to move synchronously in a vertical direction, the radiation emitted from the radiation source is confined into a sector planar beam after passing through the collimator, and is entered into the detector window after passing through the inspected human body. The radiation distribution data in lines of the image (preferably every line) collected by the detector is recorded in the memory after several milliseconds, when the scanning is finished, the image after the quick processing is shown on the display. The radiation device for the human body inspection according to the present invention can ensure that the radiation source and the detector can be operated synchronously during the whole inspection process; thereby the quality of radiation imaging is increased. Furthermore, the radiation device for the human body inspection according to the present invention is advantageous in saving cost and reducing noise.

EXPLANATION FOR REFERENCE NUMBERS

1—X-ray generator
2—guide rail I
3—guide wheel
4—steel belt I
5—steel belt II
6—guide rail II
7—detector
8—guide rail III
9—steel belt connection
10—steel belt III
11—hoist

DETAILED DESCRIPTION OF PREFERRED EMBODIMENTS

Figure 1:
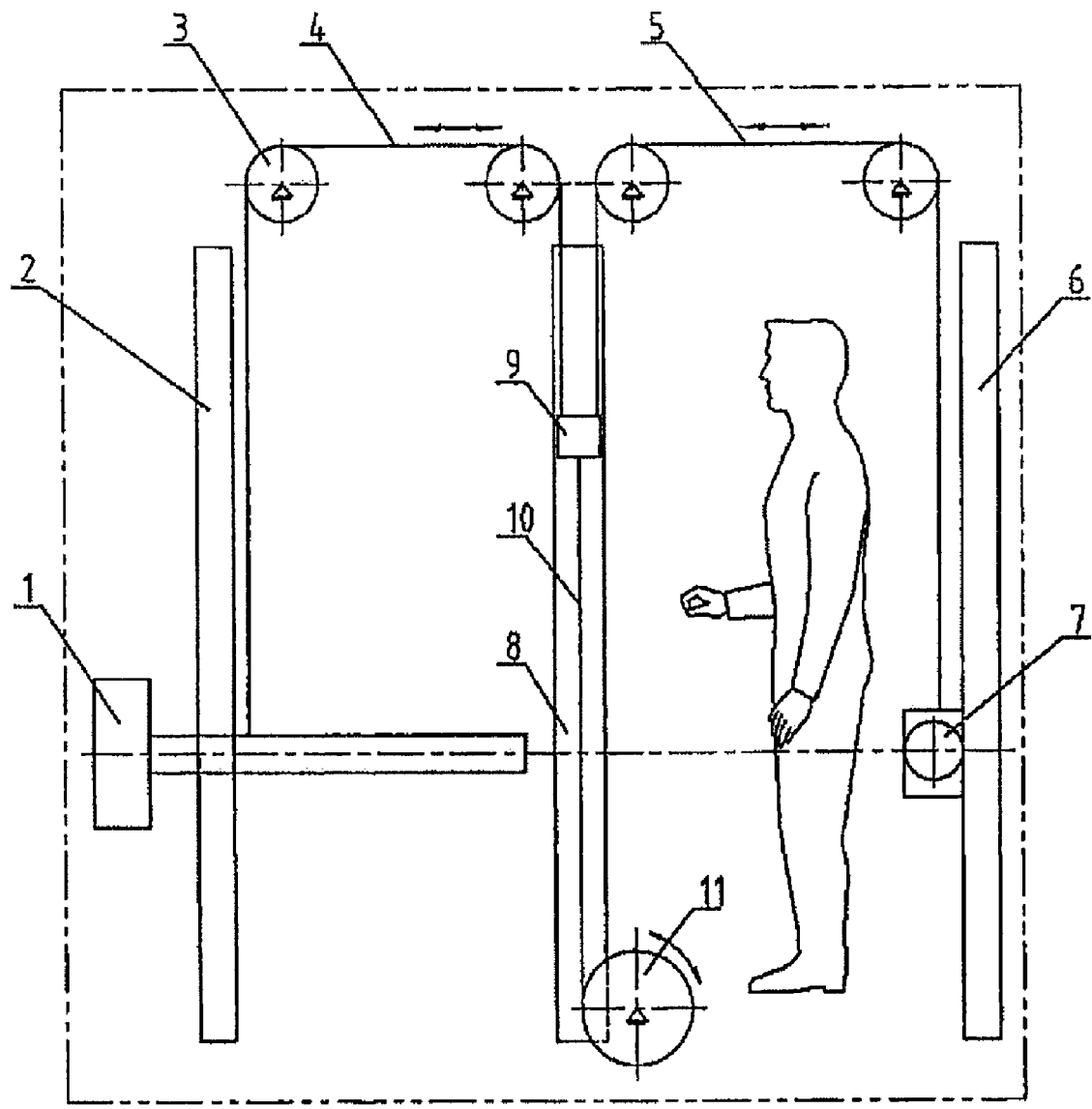
FIG. 1 is a schematic view of the radiation device for the human body inspection according to an embodiment of the present invention.

As shown in FIG. 1, the radiation device for the human body inspection includes: a X-ray generator 1 for generating radiation; a detector 7 for receiving the radiation emitting from the X-ray generator; a steel belt 4 for connecting with and for elevating or hoisting the X-ray generator 1, a steel belt 5 connected with the detector 7 and for elevating or hoisting the detector 7; and a hoist 11 for driving the X-ray generator 1 and the detector 7 synchronously through the steel belts 4 and 5, while the X-ray generator 1 is spaced from the detector 7 at a predetermined distance in the horizontal direction.

As shown in FIG. 1, the radiation device for the human body inspection further includes: a guide rail 2 for guiding the driving of the radiation device; and a guide rail 6 for guiding the driving of the detector 7.

As shown in FIG. 1, steel belts 4 and 5 are wound around the guide wheel 3 to connect with one end of the steel belt connection 9, one end of the steel belt 10 is connected with the other end of the steel belt connection 9, and the other end of the steel belt 10 is connected with the hoist 11 disposed at the lower portion of the radiation device for security inspection, so that the X-ray generator 1 and the detector 7 are synchronously lifted and dropped by the hoist 11.

The hoist 11 includes a hoisting cylinder and a motor for driving the hoisting cylinder, the steel belt 10 is connected with the hoisting cylinder. The thickness of the belt can be 0.1 mm to 1 mm, and in the present embodiment, the thickness of the belt is 0.2 mm. The width of the steel belt W is depending on the load size for hoisting the X-ray generator 1 and the detector 7, which is mainly used for removing the amount of the deformation of the steel belt caused by the force generated by the acceleration under the actuating of the steel belt, the width thereof may be from 20 mm to 200 mm. As an example, the steel belt has a width W of 30 mm in the present embodiment.

In order to ensure the synchronism of the operation, the X-ray generator 1, the receiver 7 and the steel belt connection 9 may be run along a guiding device, which can be a guiding rail, a shaft or the like. The present embodiment employs three guiding rails, so that the X-ray generator 1, the receiver 7 and the steel belt connection 9 are run along the guiding rails.

The hoist is used in above embodiment. As an alternative, a driving device including a nut, a leading screw cooperating with the nut and a motor driving the leading screw to rotate can be employed instead of the hoist. Under such situation, the steal belts 4 and 5 can be directly connected with the nut. With rotation of the leading screw, the nut is moved to move up and down, thus, the X-ray generator 1 and the receiver 7 are driven to be moved up and down. Furthermore, instead of the nut and the leading screw, a rack and a gear can be used.

Also, in above embodiment, the hoist 11 is provided at the lower portion thereof, but it also can be provided at a place where the guiding wheel 3 is located. At this time, the guiding wheel 3 is replaced by a hoist 11. Furthermore, the hoist 11 also can be provided at any place above the guiding rails 2, 6, and 8.

By using the radiation device for the human body inspection of the present invention, during the human body inspection, people can stand still and the radiation generating device and the detector are moved, or people can move and the radiation generating device and the detector are kept still. In this embodiment, people stand still and the X-ray generator and the detector are moved vertically.

Figure 2:
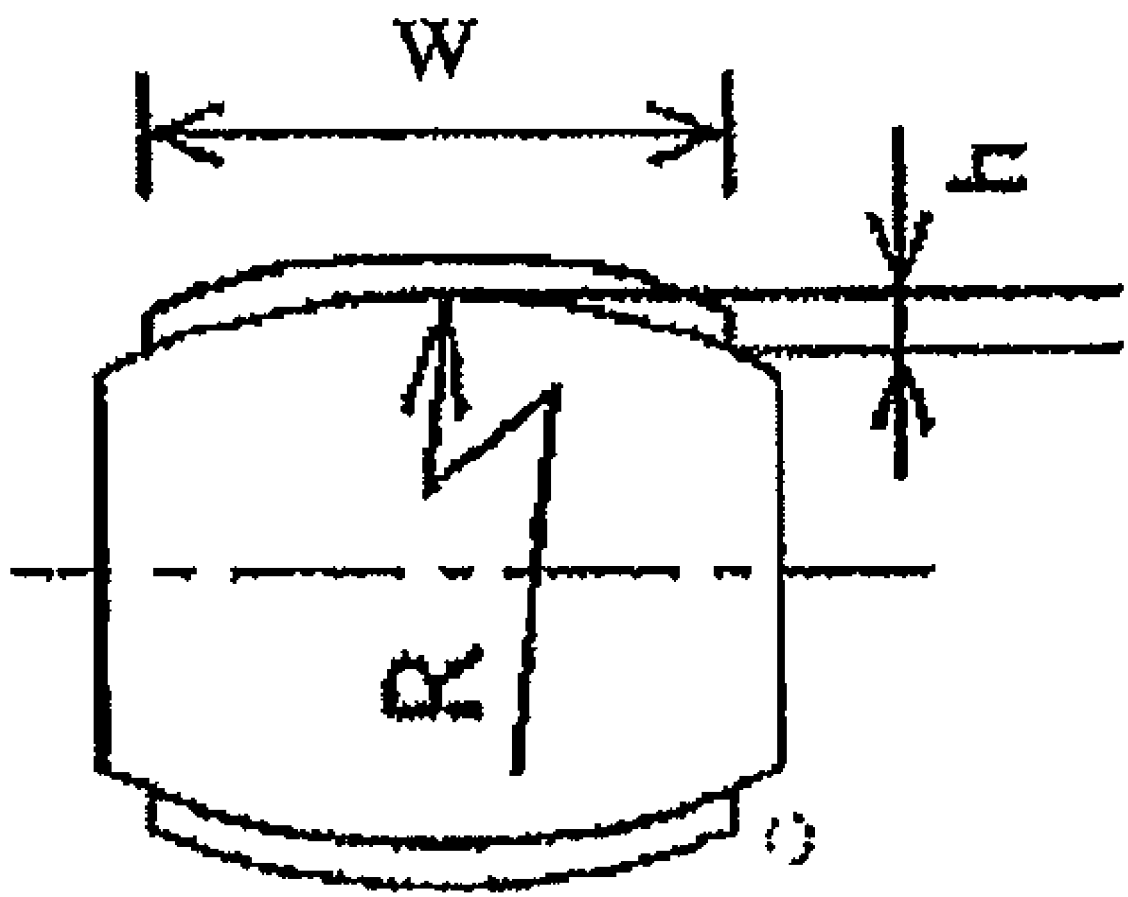
FIG. 2 is a schematic view of the belt wheel and the hoisting cylinder of the radiation device for the human body inspection according to an embodiment of the present invention.

Furthermore, in order to prevent the steel belt 4, 5, and 10 from slipping transversely when it is moved, the belt wheel 3 and the hoisting cylinder are formed in a drum shape in this embodiment, as shown in FIG. 2.

For the diameter of the belt wheel 3 and the hoisting cylinder, it can be 400 to 4000 times of the thickness of the steel belt, and it is 700 times of the thickness of the steel belt in the illustrated embodiment.

When the hoist 11 is rotated, the steel belt 4 is wound around the cylinder. Since the winding diameter may become bigger due to the effect of the thickness of the steel belt, solutions, such as reducing the thickness of the steel belt and increasing the diameter of the cylinder can be employed. In the embodiment, a solution of reducing the thickness of the steel belt is utilized, while the diameter of the cylinder is properly increased so that the number of the winding is reduced, such that the error can be reduced as much as possible.

A protection device can be added, which can prevent the X-ray generator and the detector from the damage caused by the breakage of the steel belt under some special conditions, such protection device can employ a set of additional steel rope or belt. The set of steel rope protection device can be added corresponding to the steel belt, the additional steel rope is not operated during the normal operation; however, when the steel belt is broken by accident, the steel rope is tighten so as to protect the loading thereof from the damage.

The operating principle of the radiation device for the human body inspection according to the present invention is as following:

The hoist 11 is driven by the motor to pull the steel belt member 10, and the steel belt connection 9 is moved along the guide rail 10, at the same time, the steel belts 4 and 5 are pulled. The steel belt 4 pulls the X-ray generator 1 and the steel belt 5 pulls the detector 7, the X-ray generator 1 and the detector 7 are respectively moved along the guide rails 2 and 6. As described above, the system device uses the steel belt as the transmission member to transfer the power of the hoist from one steel belt to two other steel belts at both sides through a connection, so that synchronism of loads hoisting at both sides can be ensured. At the same time, the radiation device emits the radiation; the radiation radiated from the radiation source is confined into a sector planar beam after passing through the collimator, and entered into the detector window after passing through the inspected human body. The radiation distribution data in lines of the image collected by the detector is recorded in the memory after several milliseconds, when the scanning is finished, the image through the quick processing is shown on the display.

In addition, although the steel belt is employed in above embodiment, instead of the steel belt, any other things such as flat steel rope, belt made in synthetic fiber also can be used.

What the claim is:

1. A radiation device for the human body inspection, comprising:
    an X-ray generator for radiating radiation;
    a detector for receiving the radiation radiated from the X-ray generator;
    a first flexible member connected with the X-ray generator for hoisting the X-ray generator;
    a second flexible member connected with the detector for hoisting the detector;
    a first guiding device for guiding the X-ray generator to elevate;
    a second guiding device for guiding the detector to elevate;
    a driving device for synchronously driving the X-ray generator and the detector through the first and second flexible members, and at the same time, the X-ray generator and the detector are spaced from each other a predetermined distance in a horizontal direction; and
    one or more guiding wheels, wherein said first and second flexible members are wound around said one or more guiding wheels so as to connect with the driving device.

2. The radiation device for the human body inspection as claimed in claim 1, wherein the first guiding device and the second guiding device comprise guiding rails provided vertically.

3. The radiation device for the human body inspection as claimed in claim 1, further comprises a third flexible member, and a flexible member connection, said first flexible member and said second flexible member are connected with one end of the third flexible member through the flexible member connection, wherein said driving device comprises a hoist, the other end of the third flexible member is connected with the hoist so as to drive the first and second flexible members.

4. The radiation device for the human body inspection as claimed in claim 3, further comprises a third guiding device for guiding the flexible member connection.

5. The radiation device for the human body inspection as claimed in claim 4, wherein said third guiding device comprises a guiding rail disposed vertically.

* * * * *